US011129969B2

(12) United States Patent
Pederson, Jr. et al.

(10) Patent No.: US 11,129,969 B2
(45) Date of Patent: Sep. 28, 2021

(54) LOADING TOOLS FOR USE WITH MEDICAL DEVICES

(71) Applicant: BOSTON SCIENTIFIC SCIMED, INC., Maple Grove, MN (US)

(72) Inventors: Gary John Pederson, Jr., Albertville, MN (US); Katherine Stryker Brodeen Routh, Coon Rapids, MN (US); Daniel J. Gregorich, Plymouth, MN (US); Jordan Pollack, Minneapolis, MN (US); James M. Anderson, Corcoran, MN (US); David Raab, Roseville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 508 days.

(21) Appl. No.: 15/902,619

(22) Filed: Feb. 22, 2018

(65) Prior Publication Data
US 2018/0236208 A1    Aug. 23, 2018

Related U.S. Application Data

(60) Provisional application No. 62/462,673, filed on Feb. 23, 2017.

(51) Int. Cl.
*A61M 25/06*    (2006.01)
*A61F 2/962*    (2013.01)
(Continued)

(52) U.S. Cl.
CPC ......... *A61M 25/0662* (2013.01); *A61F 2/962* (2013.01); *A61M 25/00* (2013.01);
(Continued)

(58) Field of Classification Search
CPC ...... A61F 2/9522; A61F 2/962; A61F 2/2427; A61F 2250/0067; A61F 2002/0072;
(Continued)

(56) References Cited

U.S. PATENT DOCUMENTS

| 4,306,562 A | 12/1981 | Osborne |
| 4,515,592 A | 5/1985 | Frankhouser |

(Continued)

FOREIGN PATENT DOCUMENTS

| CN | 104363891 A | 2/2015 |
| DE | 20319821 U1 | 3/2004 |

(Continued)

OTHER PUBLICATIONS

International Search Report and Written Opinion dated May 29, 2018 for International Application No. PCT/US2018/019209.

*Primary Examiner* — Manuel A Mendez
(74) *Attorney, Agent, or Firm* — Seager, Tufte & Wickhem, LLP (57) ABSTRACT

Loading tools for use with medical devices are disclosed. An example loading tool may be suitable for use with a drug-coated expandable medical device. The loading tool may include a tubular sleeve having a distal end region, a proximal end region, and a lumen extending therethrough. The distal end region may include a reduced distal tip designed to interact with a hemostasis valve having a resilient seal member.

11 Claims, 10 Drawing Sheets

(51) Int. Cl.
  *A61M 25/00* (2006.01)
  *A61M 39/06* (2006.01)
  *A61F 2/00* (2006.01)
  *A61F 2/24* (2006.01)
  *A61M 25/01* (2006.01)
  *A61F 2/95* (2013.01)

(52) U.S. Cl.
  CPC ....... *A61M 39/0693* (2013.01); *A61F 2/2427* (2013.01); *A61F 2/9522* (2020.05); *A61F 2002/0072* (2013.01); *A61F 2250/0067* (2013.01); *A61M 25/0097* (2013.01); *A61M 2025/0188* (2013.01); *A61M 2025/0681* (2013.01)

(58) Field of Classification Search
  CPC .............. A61M 25/0662; A61M 25/00; A61M 39/0693; A61M 25/0097; A61M 2025/0188; A61M 2025/0681
  See application file for complete search history.

(56) References Cited

U.S. PATENT DOCUMENTS

| | | |
|---|---|---|
| 4,983,168 A | 1/1991 | Moorehead |
| 5,549,551 A | 8/1996 | Peacock et al. |
| 5,674,192 A | 10/1997 | Sahatjian et al. |
| 5,769,816 A | 6/1998 | Barbut et al. |
| 6,093,194 A | 7/2000 | Mikus et al. |
| 6,221,081 B1 | 4/2001 | Mikus et al. |
| 6,287,280 B1 | 9/2001 | Lampropoulos et al. |
| 6,517,569 B2 | 2/2003 | Mikus et al. |
| 6,537,254 B1 | 3/2003 | Schock et al. |
| 7,105,013 B2 | 9/2006 | Durcan |
| 8,162,890 B2 | 4/2012 | Amisar et al. |
| 2002/0062129 A1 | 5/2002 | Mikus et al. |
| 2003/0050604 A1 | 3/2003 | Lui et al. |
| 2004/0093005 A1 | 5/2004 | Durcan |
| 2009/0306591 A1 | 12/2009 | Amisar et al. |
| 2011/0208284 A1 | 8/2011 | Hofmann et al. |
| 2011/0224678 A1 | 9/2011 | Gabbay |
| 2012/0296313 A1 | 11/2012 | Andreacchi et al. |
| 2013/0303983 A1* | 11/2013 | Barbick .................. A61P 35/00 604/103.02 |
| 2014/0074022 A1 | 3/2014 | Gunderson et al. |
| 2017/0367824 A1* | 12/2017 | Jelle ..................... A61M 25/10 |

FOREIGN PATENT DOCUMENTS

| | | |
|---|---|---|
| JP | 2003525660 A | 9/2003 |
| JP | 2014516691 A | 7/2014 |
| WO | 01/02045 A | 1/2001 |
| WO | 0117587 A1 | 3/2001 |
| WO | 2007/132444 A2 | 11/2007 |
| WO | 2016115361 A1 | 7/2016 |
| WO | WO-2016115361 A1 * | 7/2016 ........... A61F 2/2433 |

* cited by examiner

FIG. 10 a plurality of axially-extending slots arranged about the reduced distal tip and wherein disposing the reduced distal tip into a resilient seal member of the valve includes disposing the axially-extending slots into the resilient seal member.

LOADING TOOLS FOR USE WITH MEDICAL DEVICES

CROSS-REFERENCE TO RELATED APPLICATIONS

This application claims the benefit of priority under 35 U.S.C. § 119 to U.S. Provisional Application Ser. No. 62/462,673, filed Feb. 23, 2017, the entirety of which is incorporated herein by reference.

TECHNICAL FIELD

The present disclosure pertains to medical devices, and methods for manufacturing medical devices. More particularly, the present disclosure pertains to loading tools for use with medical devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a loading tool for use with a drug-coated expandable medical device. The loading tool comprises: a tubular sleeve having a distal end region, a proximal end region, and a lumen extending therethrough; wherein the distal end region includes a reduced distal tip designed to interact with a hemostasis valve having a resilient seal member, the reduced distal tip having a structure with a reduced dimension that allows the reduced distal tip to be passed into a proximal end of the hemostasis valve in such a way to reduce displacement of the resilient seal member while the drug-coated expandable medical device is passed therethrough and that also reduces an amount of force applied by the resilient seal member onto the drug-coated expandable medical device such that a drug coating on the drug-coated expandable medical device substantially remains adhered to the drug-coated expandable medical device when passing the drug-coated expandable medical device through the reduced distal tip and through the resilient seal member; wherein the lumen is designed to hold the drug-coated expandable medical device while the reduced distal tip is brought into contact with and passes at least partially through the resilient seal member, the lumen also being a passageway for passing the drug-coated expandable medical device from a position proximal of the resilient seal member, through the resilient seal member, and into a body lumen; and wherein the proximal end region includes a proximal entry port designed to allow the drug-coated expandable medical device into the lumen and allow the drug-coated expandable medical device to be passed through the reduced distal tip, through the resilient seal member, and into the body lumen.

Alternatively or additionally to any of the embodiments above, the reduced distal tip comprises a single axially-extending slit disposed along the reduced distal tip.

Alternatively or additionally to any of the embodiments above, the reduced distal tip comprises a plurality of axially-extending slots arranged about the reduced distal tip.

Alternatively or additionally to any of the embodiments above, at least some of the axially-extending slots extend through a tube wall of the tubular sleeve.

Alternatively or additionally to any of the embodiments above, at least some of the axially-extending slots extend through only partially through a tube wall of the tubular sleeve.

Alternatively or additionally to any of the embodiments above, further comprising a stop member disposed adjacent to the axially-extending slots.

Alternatively or additionally to any of the embodiments above, the reduced distal tip comprises a beveled distal end.

Alternatively or additionally to any of the embodiments above, the tubular sleeve comprises a tubular body having a first section and a second section separable from the first section, the second section having a flared distal end region, the first section including the reduced distal region with a smaller outer diameter than an outer diameter of the flared distal end region of the second section.

Alternatively or additionally to any of the embodiments above, the drug-coated expandable medical device comprises a drug-coated balloon.

Alternatively or additionally to any of the embodiments above, the drug-coated expandable medical device comprises a drug-coated stent.

A method for loading an expandable medical device into a valve is disclosed. The method comprises: disposing a loading tool about the expandable medical device, the loading tool comprising a tubular body having a proximal end region and a distal end region with a reduced distal tip; disposing the reduced distal tip into a resilient seal member of the valve; advancing the expandable medical device through the reduced distal tip and through the resilient seal member; and removing the reduced distal tip from the resilient seal member.

Alternatively or additionally to any of the embodiments above, the expandable medical device comprises a drug-coated expandable medical device, and wherein advancing the expandable medical device through the reduced distal tip and through the resilient seal member reduces an amount of force applied by the resilient seal member onto the drug-coated expandable medical device such that a drug coating on the drug-coated expandable medical device substantially remains adhered to the drug-coated expandable medical device when passing the drug-coated expandable medical device through the reduced distal tip and through the resilient seal member.

Alternatively or additionally to any of the embodiments above, the expandable medical device comprises a drug-coated balloon.

Alternatively or additionally to any of the embodiments above, the expandable medical device comprises a drug-coated stent.

Alternatively or additionally to any of the embodiments above, the reduced distal tip comprises a plurality of axially-extending slots arranged about the reduced distal tip and wherein disposing the reduced distal tip into a resilient seal member of the valve includes disposing the axially-extending slots into the resilient seal member.

Alternatively or additionally to any of the embodiments above, the reduced distal tip further comprises a stop member disposed adjacent to the axially-extending slots.

Alternatively or additionally to any of the embodiments above, the reduced distal tip comprises a beveled distal end and wherein disposing the reduced distal tip into a resilient seal member of the valve includes disposing the beveled distal end into the resilient seal member.

Alternatively or additionally to any of the embodiments above, the tubular sleeve comprises a tubular body having a first section and a second section separable from the first section, wherein the second section has a flared distal end region, wherein the first section includes the reduced distal tip, and wherein disposing the reduced distal tip into a resilient seal member of the valve includes separating the first section from the second section and reduced distal tip of the first section into the resilient seal member.

A medical device assembly is disclosed. The assembly comprises: a balloon catheter having an expandable balloon; a stent disposed along the balloon catheter; a drug coating disposed along the stent; a loading tool disposed about the stent; and wherein the loading tool comprises: a tubular sleeve having a distal end region, a proximal end region, and a lumen extending therethrough, wherein the distal end region includes a reduced distal tip designed to interact with a hemostasis valve having a resilient seal member, the reduced distal tip having a structure with a reduced dimension that allows the reduced distal tip to be passed into a proximal end of the hemostasis valve in such a way to reduce displacement of the resilient seal member while the stent is passed therethrough and that also reduces an amount of force applied by the resilient seal member onto the stent such that the drug coating on the stent substantially remains adhered to the stent device when passing the stent through the reduced distal tip and through the resilient seal member, wherein the lumen is designed to hold the stent while the reduced distal tip is brought into contact with and passes at least partially through the resilient seal member, the lumen also being a passageway for passing the stent from a position proximal of the resilient seal member, through the resilient seal member, and into a body lumen, and wherein the proximal end region includes a proximal entry port designed to allow the balloon into the lumen and allow the stent to be passed through the reduced distal tip, through the resilient seal member, and into the body lumen.

Alternatively or additionally to any of the embodiments above, the reduced distal tip comprises a plurality of axially-extending slots arranged about the reduced distal tip.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, balloon catheter, stent delivery system, interventional device, or the like in a blood vessel. Because fluid under pressure (e.g., blood) is present within the blood vessel, the fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device. This may include a hemostasis valve that can be secured to a guide catheter, a hemostasis valve that can be secured to an introducer or other medical device, a hemostasis valve on the proximal end of an introducer, or the like.

A variety of different hemostasis valve designs may be used. At least some of these designs may include a resilient seal member with one or more slits or openings formed therein that allow a device to be passed therethrough. The opening or openings are designed to deform when the device is passed therethrough in a manner that opens up the resilient seal member sufficiently to allow the medical device to pass while also conforming to the outer surface of the medical device in order to effect a sufficient seal. When passing a medical device through the resilient seal member, it can be appreciated that the resilient seal may exert a force onto the medical device. In many cases, the forces exerted on the medical device may have little or no impact on the medical device. However, in some instances, if the hemostasis valve includes a resilient seal member with a single, relatively small opening, the force exerted on the medical device could be sufficient to remove or partially remove a coating (e.g., a therapeutic coating disposed along an expandable medical device such as a balloon or stent) from the medical device. It may be desirable to limit forces between the resilient seal member and the medical device. By limiting these forces, the amount of the coating and/or drug that may be removed from the medical device during the passing of the medical device through the resilient seal member may be reduced or otherwise eliminated. In addition, by reducing the forces, it is also less likely that the medical device may cause the resilient seal to be torn or otherwise deformed in a way that cannot be recovered when the medical device is passed through the resilient seal member.

Disclosed herein are loading tools that may be used with medical devices. The loading tools are designed so that a medical device can be passed through a number of different hemostasis valves. For example, the loading tools disclosed herein are designed so that a medical device can be passed through a resilient seal member (e.g., including a resilient seal member with a single, relatively small opening) in a manner that reduces the forces applied by the resilient seal member on the medical device. This may reduce or eliminate the likelihood that a coating/drug may be removed from the medical device, may reduce or eliminate the likelihood that a resilient seal may be torn or otherwise deformed in a way that cannot be recovered, and/or provide additional benefits. In addition, the loading tools disclosed herein also allows a medical device to be loaded into a hemostasis valve while the medical device (e.g., a drug coated stent, a drug coated balloon, etc.), particularly a portion of the medical device that includes a drug coating, is covered or otherwise shielded from contact by the clinician.

Figure 1:
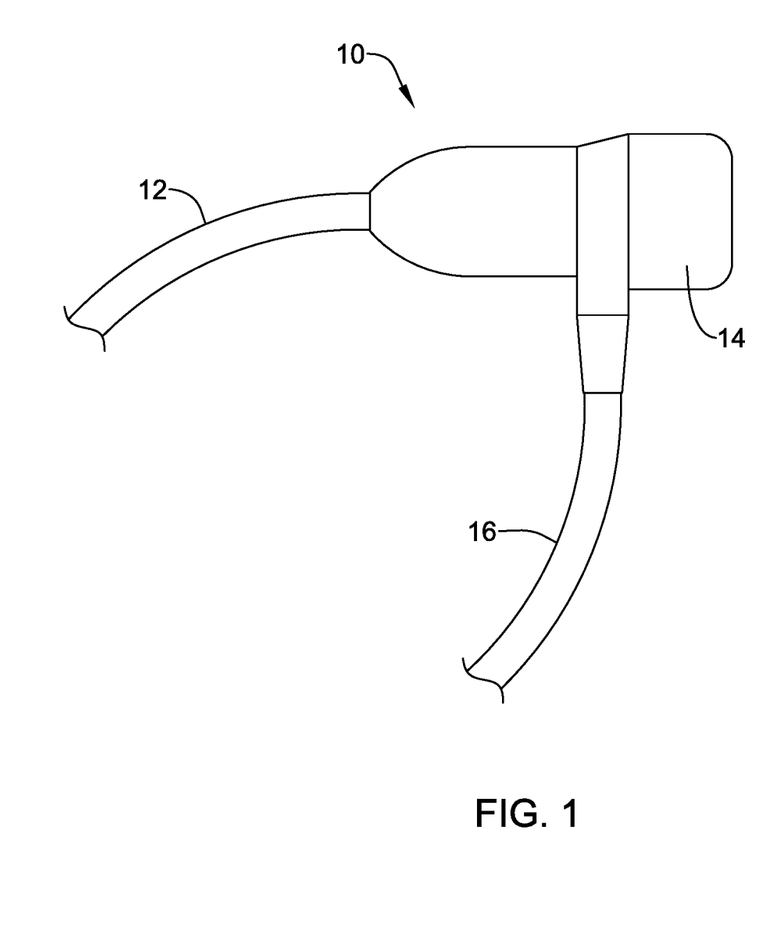
FIG. 1 is a side view of an example hemostasis valve assembly.
Figure 2:
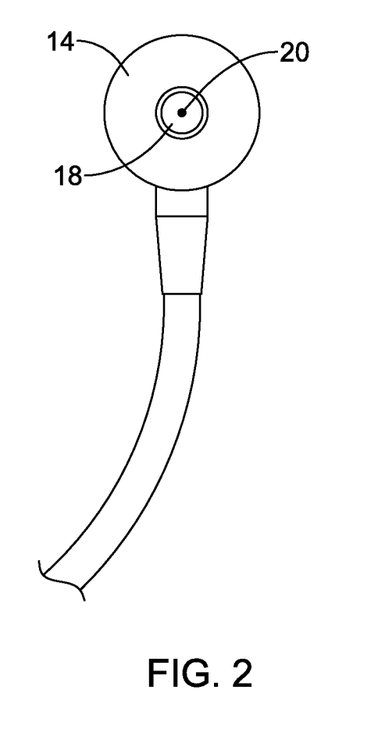
FIG. 2 is an end view of an example hemostasis valve assembly.

FIG. 1 illustrates an example hemostasis valve assembly 10. In this example, the hemostasis valve assembly 10 includes an introducer sheath 12 with a hemostasis valve 14 disposed at a proximal end of the introducer sheath 12. The hemostasis valve 14 may have a side port 16 that may be used to infuse fluids or the like. As shown in FIG. 2, the hemostasis valve 14 may include a resilient seal member 18 having an opening 20 formed therein. In this example, the hemostasis valve 14 includes only a single opening 20. However, other hemostasis valves 14 may have differing arrangements including slits, cross-slits, star-shaped slits, or the like. In general, the opening 20 may be designed to deform when a medical device is passed therethrough in a manner that allows the medical device to pass therethrough while also conforming to the outer surface of the medical device in order to effect a sufficient seal.

Figure 3:
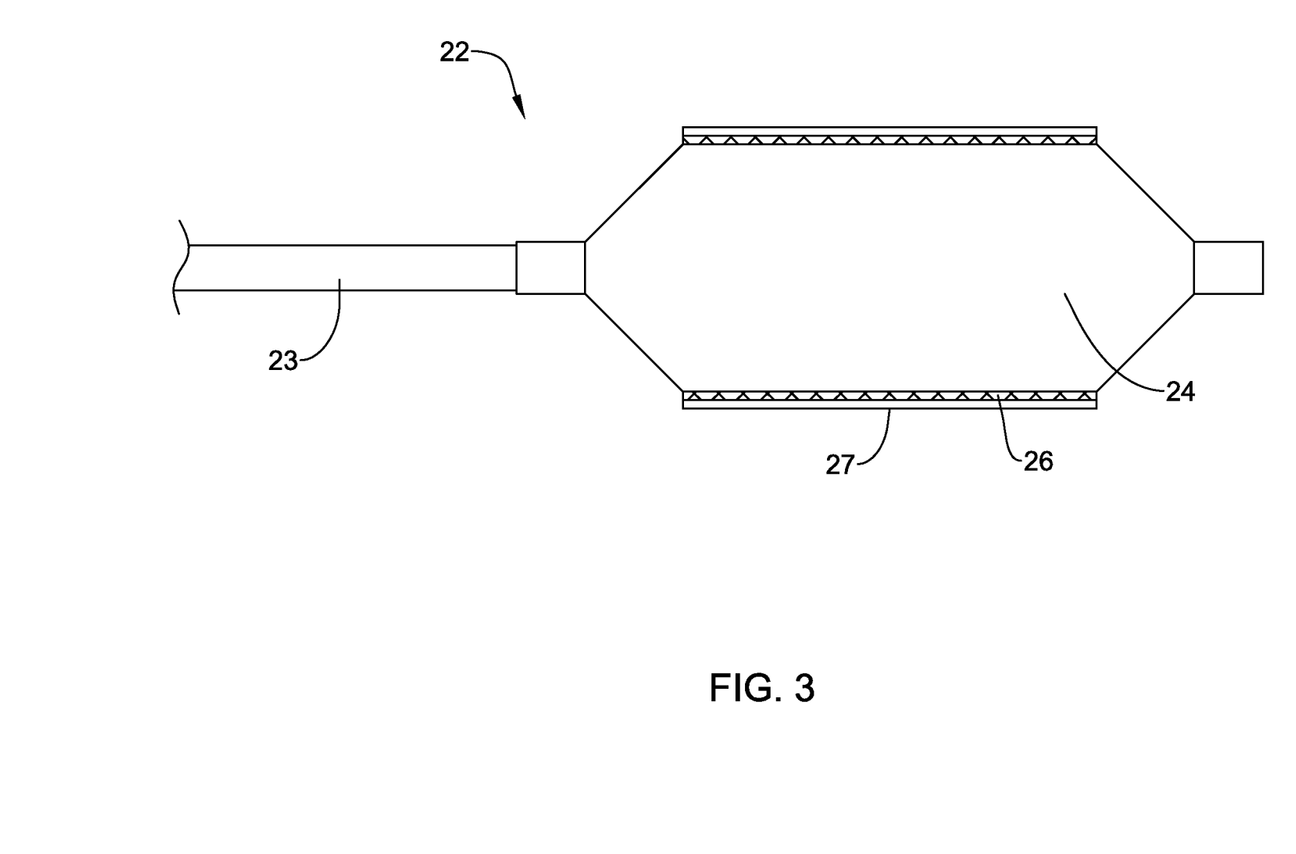
FIG. 3 is a side view of an example medical device.

An example medical device 22 that may be passed through the resilient seal member 18 is shown in FIG. 3. The example medical device 22 may take the form of a stent delivery system including a catheter shaft 23, an expandable balloon 24 coupled to the catheter shaft 23, an expandable stent 26 coupled the balloon 24, and a coating 27 (e.g., a therapeutic or drug coating 27) coupled to the stent 26. This is just one example. Other medical devices contemplated include balloon catheters, self-expanding or other stent delivery systems, drug coated balloons, systems for delivering other implantable medical devices including prosthetic valves, catheters, or the like.

Figure 4:
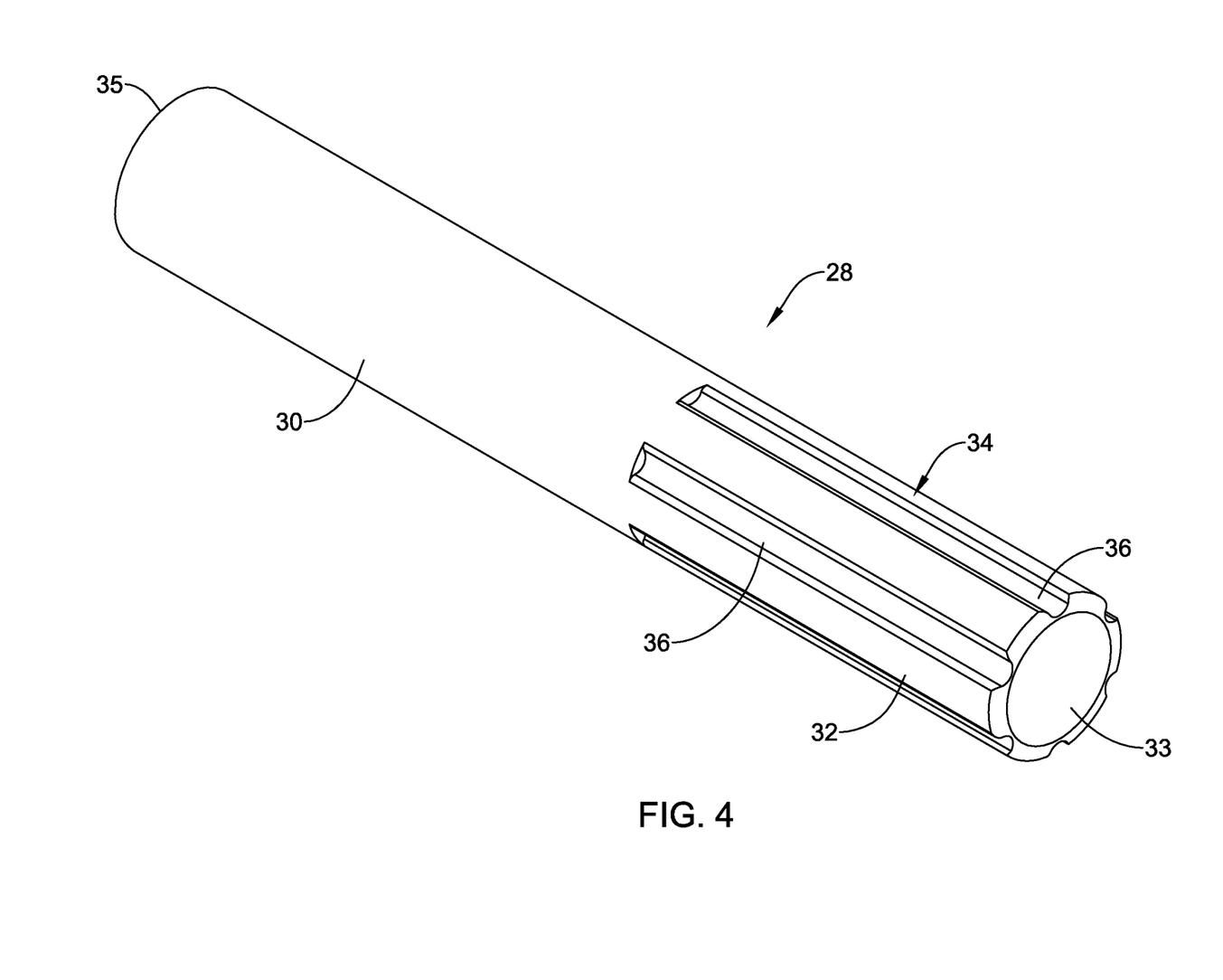
FIG. 4 is a perspective view of an example loading tool.

In order to efficiently navigate the medical device 22 through the resilient seal member 18 of the hemostasis valve 14, a loading tool 28 may be utilized such as the loading tool 28 depicted in FIG. 4. The loading tool 28 may take the form of a tubular body or sleeve that includes a proximal end region 30, a distal end region 32, and a lumen 33 extending at least partially therethrough. In general, the loading tool 28 is designed to be disposed at least partially about the medical device 22. For example, the loading tool 28 may be disposed about portions of the catheter shaft 23, portions or all of the balloon 24, portions or all of the stent 26, and/or portions or all of the coating 27.

The distal end region 32 may include a reduced distal tip 34. In general, the reduced distal tip 34 is designed to interact with the hemostasis valve 14. For example, the reduced distal tip 34 may have a structure or arrangement with a reduced dimension that allows the reduced distal tip 34 to be passed into a proximal end of the hemostasis valve 14 in such a way to reduce displacement of the resilient seal member 18 while the medical device 22 is passed therethrough and that also reduces an amount of force applied by the resilient seal member 18 onto the medical device 22 such that, the coating 27 (e.g., a drug coating) on the medical device 22 substantially remains adhered or coupled to the medical device 22 when passing the medical device 22 through the reduced distal tip 34 and through the resilient seal member 18.

The loading tool 28 may include other structural features and/or components. For example, the lumen 33 of the loading tool 28 may be designed to hold the medical device 22 while the reduced distal tip 34 is brought into contact with and passes at least partially through the resilient seal member 18. The lumen 33 may also be understood to be a passageway for passing the medical device 22 from a position proximal of the resilient seal member 18, through the resilient seal member 18, and into a body lumen such as a blood vessel. The proximal end region 30 may include a proximal entry port 35 designed to allow the medical device 22 into the lumen 33 and allow the medical device 22 to be passed through the reduced distal tip 34, through the resilient seal member 18, and into the body lumen. In some instances, the proximal entry port 35 may be an opening at the proximal end of the proximal end region 30 that provides access to the lumen 33. Alternatively, the proximal entry port 35 may be an opening in the side wall of the loading tool 28 that provides access to the lumen 33.

The form of the reduced distal tip 34 may vary. For example, the reduced distal tip 34 may include one or more axially-extending slots 36 disposed about the reduced distal tip 34. The number, form, arrangement, and the like of the axially-extending slots 36 can vary. For example, the reduced distal tip 34 may include one, two, three, four, five, six, seven, eight, or more axially-extending slots 36. The axially-extending slots 36 may be evenly spaced about the reduced distal tip 34 or unevenly spaced. The axially-extending slots 36 may all have the same length or one or more of the axially-extending slots 36 may differ in length. In some instances, one or more of the axially-extending slots 36 may extend only partially through the wall of the reduced distal tip 34. For example, all of the axially-extending slots 36 may extend only partially through the wall of the reduced distal tip 34, as shown in FIG. 4. In some of these and in other instances, one or more of the axially-extending slots 36 may extend through (e.g., completely through) the wall of the reduced distal tip 34. For example, all of the axially-extending slots 36 may extend through the wall of the reduced distal tip 34. The axially-extending slots 36 may reduce the amount of surface area about the reduced distal tip 34 that contacts the resilient seal member 18 when extending the reduced distal tip 34 through the resilient seal member 18. This may allow the reduced distal tip 34 to efficiently pass through the resilient seal member 18 in a manner that reduces the likelihood of damage being caused to the resilient seal member 18. In some instances, the wall surfaces of the reduced distal tip 34 adjacent to the axially-extending slots 36 may have rounded or chamfered edges. The distal end of the reduced distal tip 34 may also have a tapered or rounded edge. Alternatively, the wall surfaces and/or the distal end of the reduced distal tip 34 may have more squared off edges. Other shapes and/or variations are contemplated.

Figure 5:
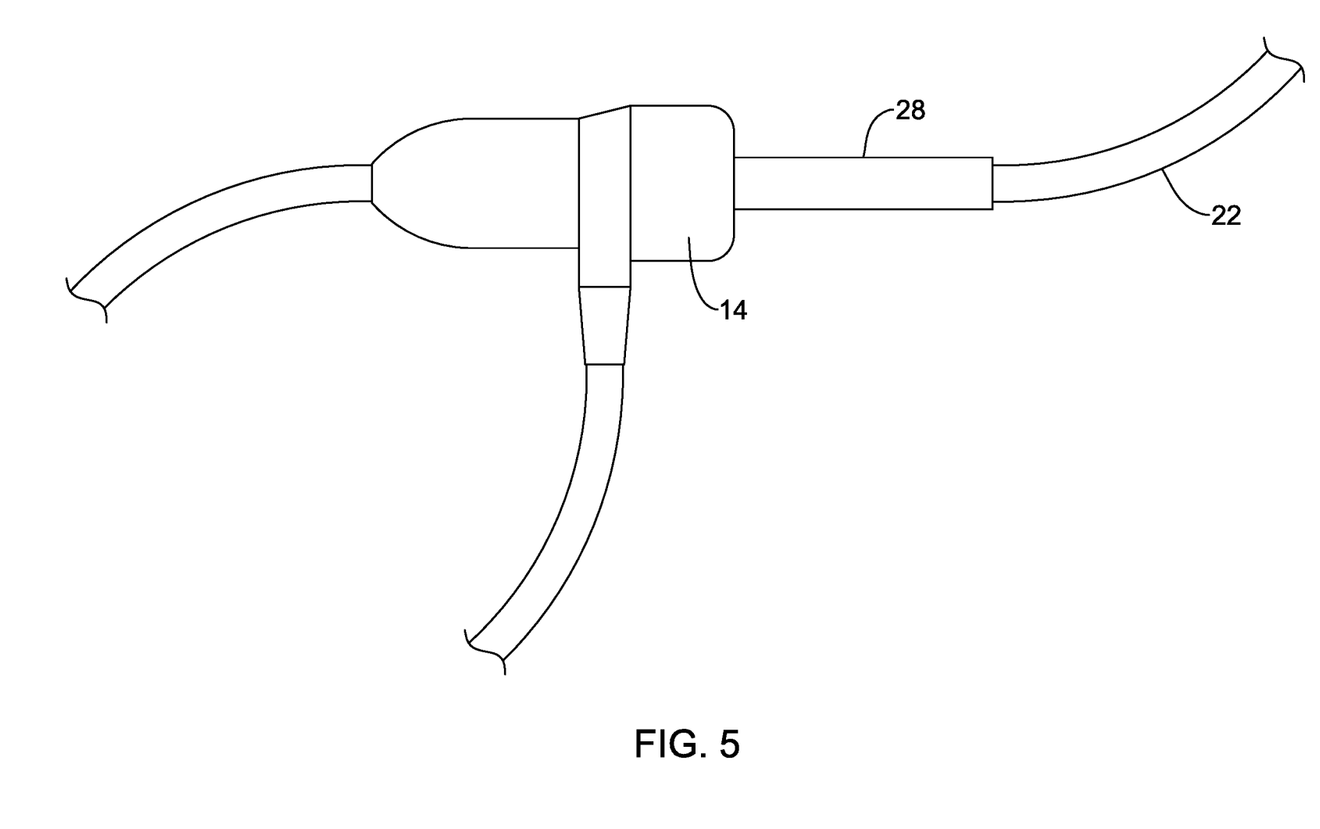
FIG. 5 is a plan view of an example loading tool being used with an example medical device and with a hemostasis valve assembly.

In use, the medical device 22 may be disposed at least partially within the loading tool 28. This may include removing the medical device 22 from its packaging, which may include removing a balloon protector from the balloon 24. Then the proximal end of the medical device 22 may be disposed within the lumen 33 by passing the proximal end of the medical device 22 through the reduced distal tip 34 of the loading tool 28 (e.g., "back loading") or extending the distal end of the medical device 22 into the lumen 33 by passing the distal end of the medical device 22 through the proximal entry port 35. With the medical device 22 suitably arranged within the loading tool 28 (e.g., with the balloon 24, stent 26, and coating 27 disposed within the lumen 33), the reduced distal tip 34 may be engaged with and at least partially extend into or through the resilient seal member 18 as depicted in FIG. 5. The medical device 22 can then be urged distally through the loading tool 28, through the resilient seal member 18, into the introducer sheath 12, and into the body lumen (e.g., a blood vessel). When the medical device 22 is passed in the desired manner through the resilient seal member 18, the loading tool 28 can be proximally retracted from the resilient seal member 18. In some instances, the loading tool 28 can also be removed from the catheter shaft 23. This may include cutting the loading tool 28, splitting the loading tool 28 along a perforation or line of weakness, or otherwise pulling the loading tool 28 from the catheter shaft 23. Alternatively, the loading tool 28 can be left disposed along the catheter shaft 23 and, ultimately, can be removed when the medical device 22 is removed from the body lumen.

Figure 6:
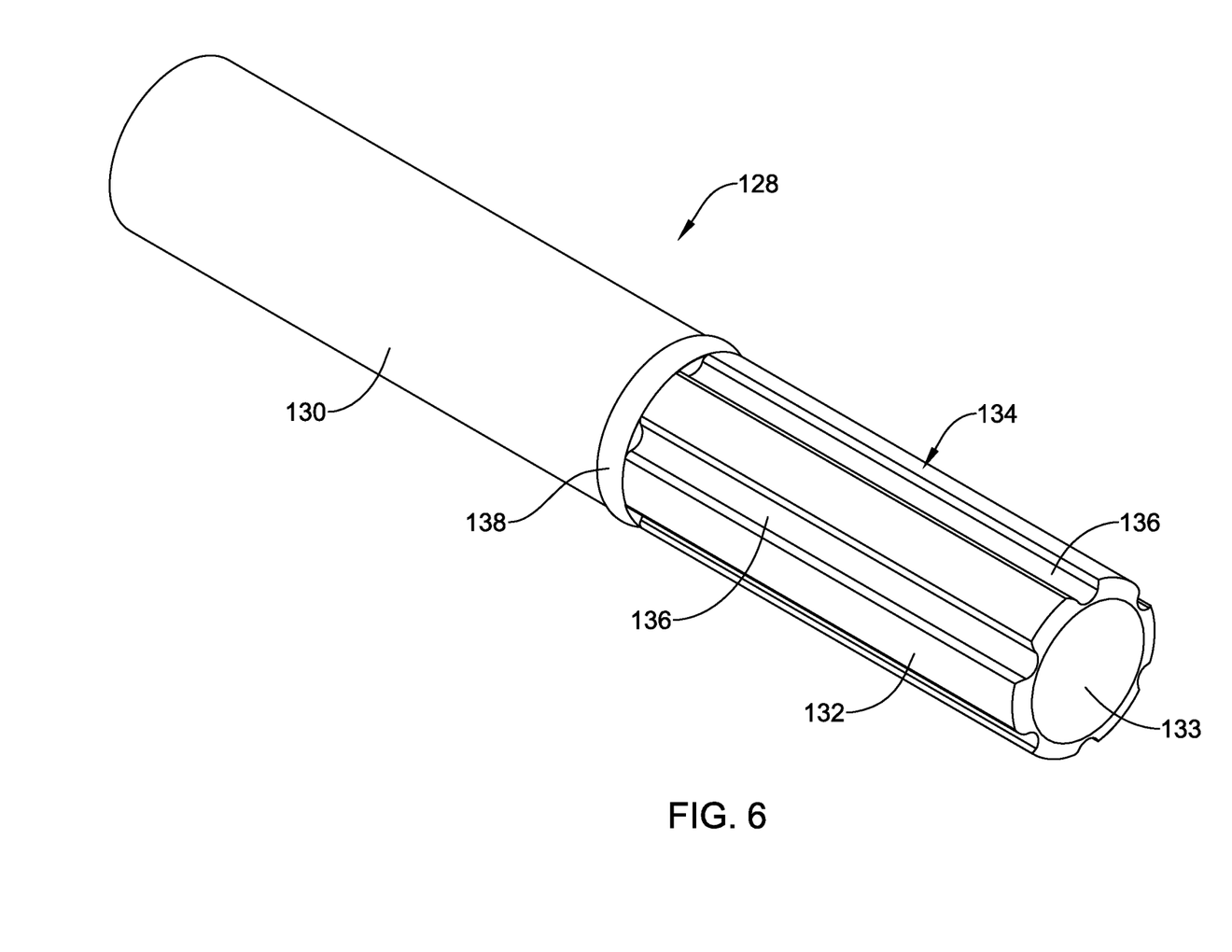
FIG. 6 is a perspective view of an example loading tool.

FIG. 6 illustrates another example loading tool 128 that may be similar in form and function to other loading tools disclosed herein. The loading tool 128 may include a proximal end region 130, a distal end region 132, and a lumen 133. The distal end region 132 may include a reduced distal tip 134. In this example, the reduced distal tip 134 may include one or more axially-extending slots 136 disposed about the reduced distal tip 134. The axially-extending slots 136 may be similar to the axially-extending slots 136 disposed about the reduced distal tip 34 of the loading tool 28. In addition, the loading tool 128 may include a stop member 138. The stop member 138 may be disposed adjacent to the axially-extending slots 136. The stop member 138 may be designed to engage the proximal end of the hemostasis valve 14 and stop any further advancement of the reduced distal tip 34 through the resilient seal member 18 and/or the hemostasis valve 14.

Figure 7:
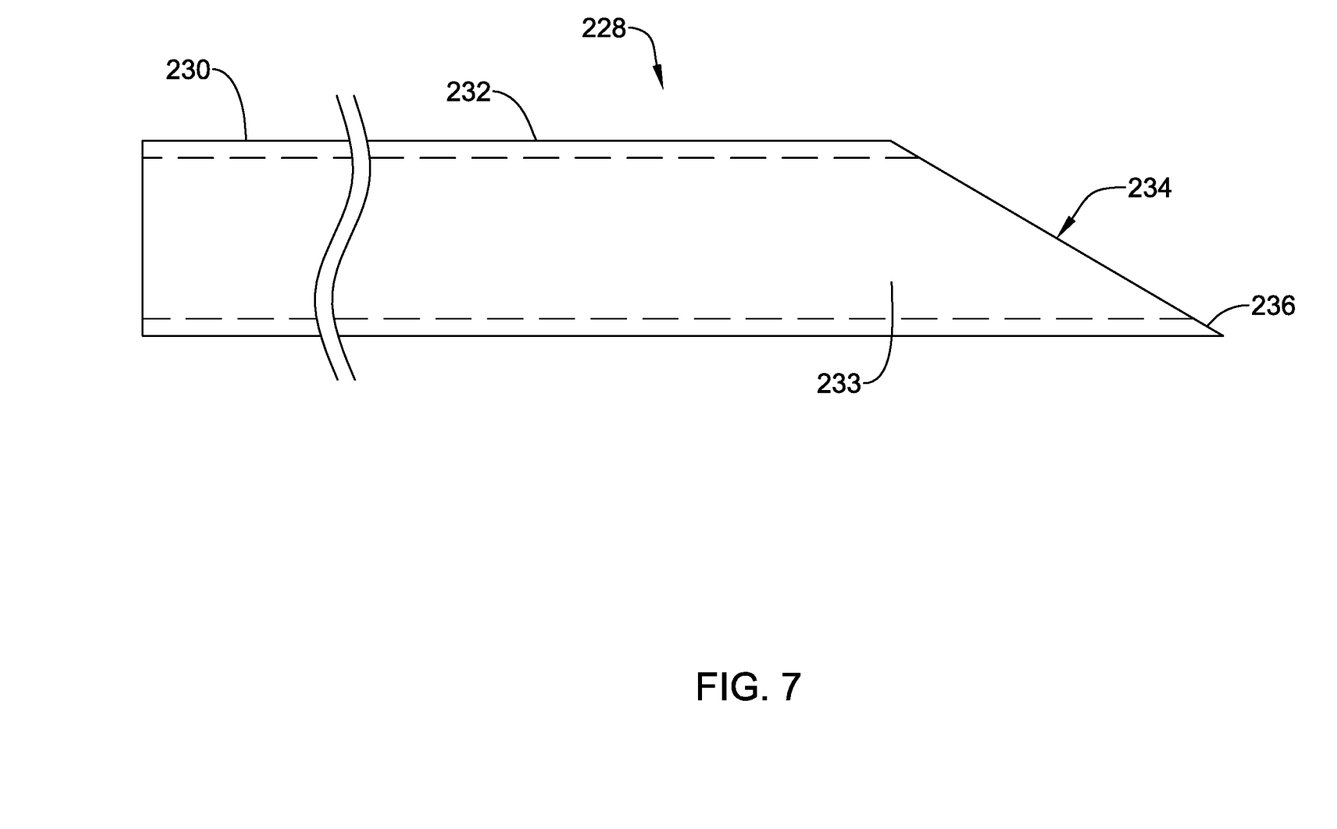
FIG. 7 is a side view of an example loading tool.

FIG. 7 illustrates another example loading tool 228 that may be similar in form and function to other loading tools disclosed herein. The loading tool 228 may include a proximal end region 230, a distal end region 232, and a lumen 233. The distal end region 232 may include a reduced distal tip 234. In this example, the reduced distal tip 234 may include a beveled distal end 236. The beveled distal end 236 may be designed to engage the resilient seal member 18 so that the medical device 22 can efficiently pass therethrough.

Figure 8:
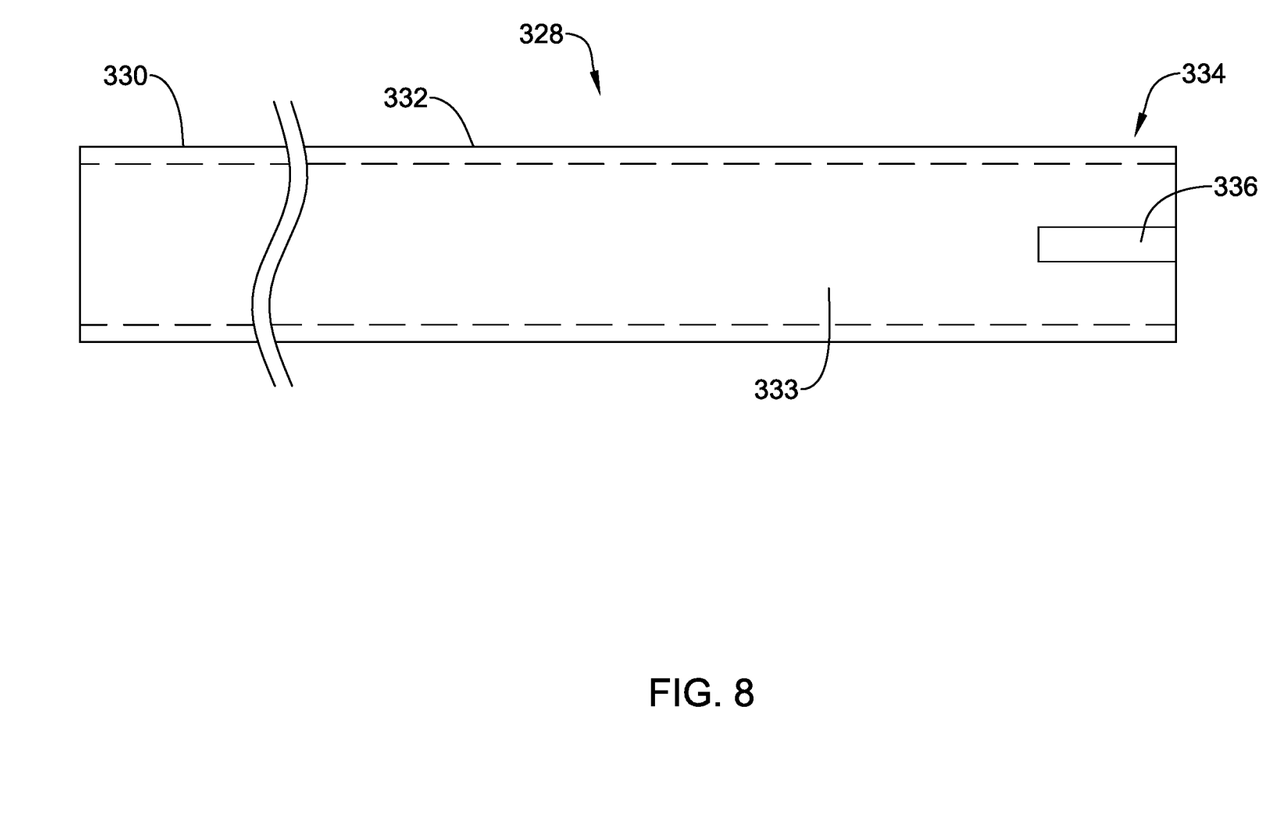
FIG. 8 is a side view of an example loading tool.

FIG. 8 illustrates another example loading tool 328 that may be similar in form and function to other loading tools disclosed herein. The loading tool 328 may include a proximal end region 330, a distal end region 332, and a lumen 333. The distal end region 332 may include a reduced distal tip 334. In this example, the reduced distal tip 334 may include a single axial slit 336. The single axial slit 336 may extend completely through or only partially through the wall of the reduced distal tip 334. In at least some instances, the axial slit 336 may allow the reduced distal tip 334 to be partially reduced or collapsed so as to facilitate insertion of the reduced distal tip 334 into the hemostasis valve 14 (e.g., into the resilient seal member 18).

Figure 9:
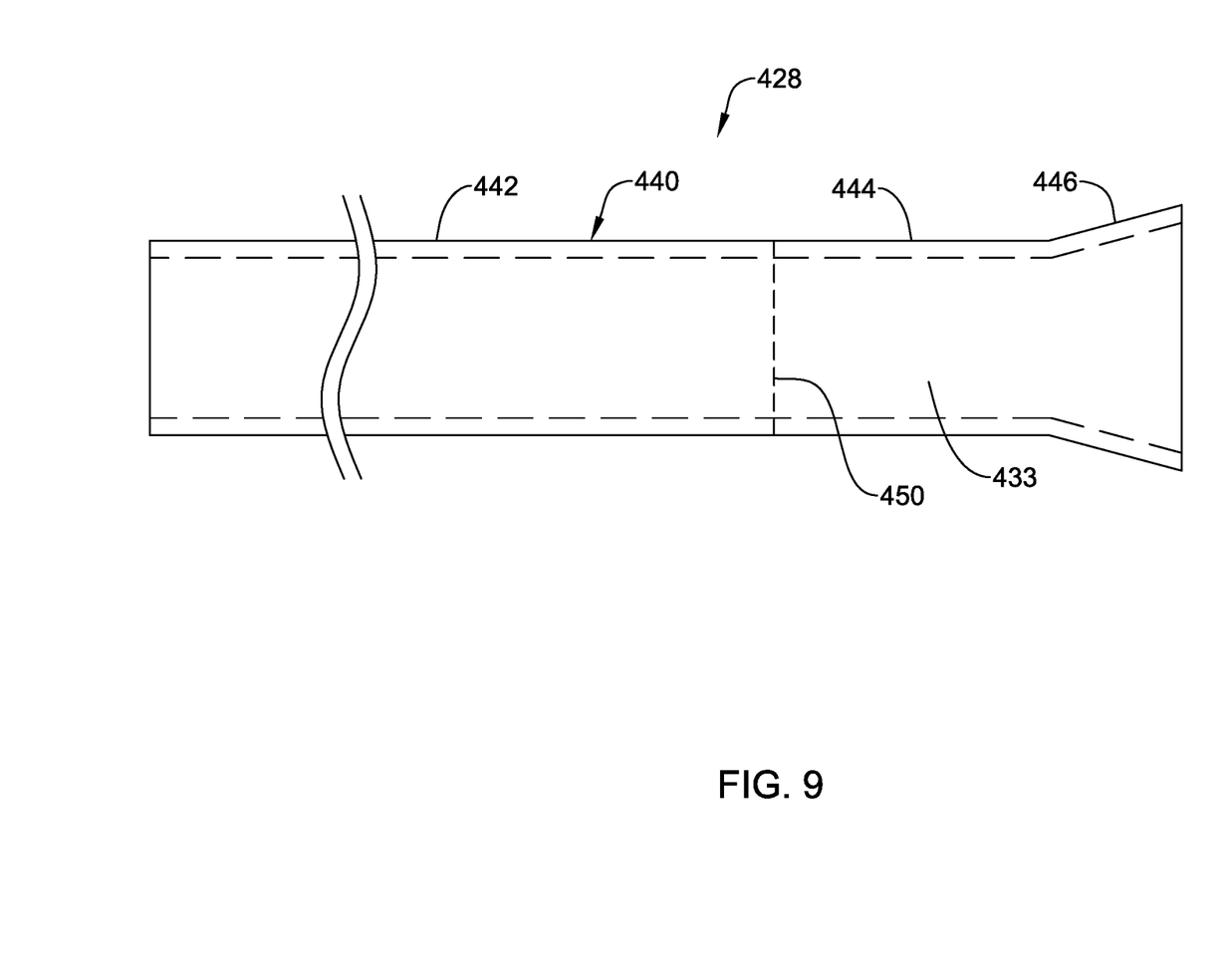
FIGS. 9-10 are side views of an example loading tool.
Figure 10:
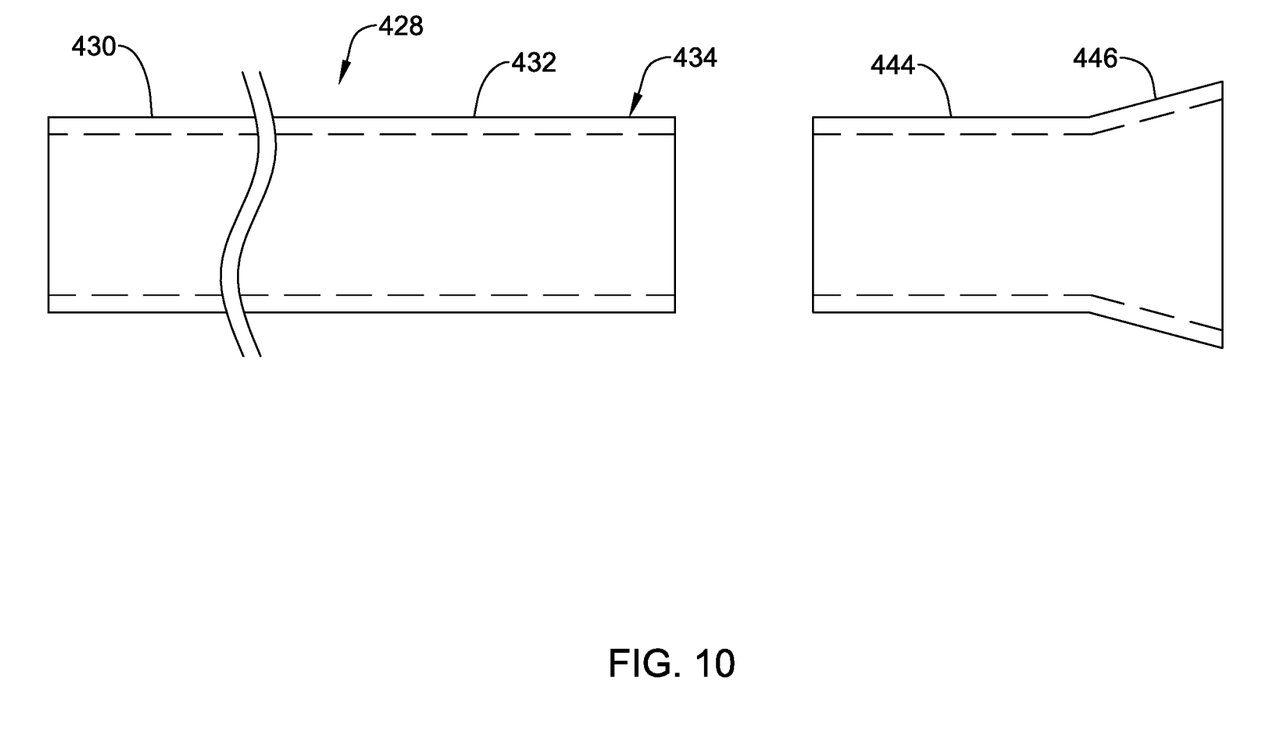

FIGS. 9 and 10 illustrates another example loading tool 428 that may be similar in form and function to other loading tools disclosed herein. The loading tool 428 may include a tubular body 440 having a first section 442, a second section 444 separable from the first section 442, and a lumen 433. The second section 444 may have a flared distal end region 446. In some instances, the loading tool 428 may be a balloon protector that is disposed about the balloon 24. The first section 442 may include a proximal end region 430, a distal end region 432 with a reduced distal tip 434. The reduced distal tip 434 may have a smaller outer diameter than an outer diameter of the flared distal end region 446 of the second section 444.

To use the loading tool 428, the first section 442 may be separated from the second section 444. This may include simply pulling the sections 442/444 apart, separating the sections 442/444 at a perforation or line of weakness 450, cutting apart the sections 442/444, or the like as depicted in FIG. 10. Removing the second section 444 from the first section 442 may define the reduced distal tip 434. The reduced distal tip 434 can be inserted into the proximal end of the hemostasis valve 14 (e.g., into and/or through the resilient seal member 18) and the medical device can be advanced through the reduced distal tip 434, through the resilient seal member 18, and into the body lumen.

The materials that can be used for the various components of the loading tool 28 (and/or other loading tools disclosed herein) may include those commonly associated with medical devices. For simplicity purposes, the following discussion makes reference to the loading tool 28. However, this is not intended to limit the devices and methods described herein, as the discussion may be applied to other similar loading tools or devices disclosed herein.

The loading tool 28 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A loading tool for use with a drug-coated expandable medical device, the loading tool comprising:
    a tubular sleeve having a distal end region, a proximal end region, and a lumen extending therethrough;
    wherein the distal end region includes a reduced distal tip designed to interact with a hemostasis valve having a resilient seal member, the reduced distal tip having a structure with a reduced dimension that allows the reduced distal tip to be passed into a proximal end of the hemostasis valve in such a way to reduce displacement of the resilient seal member while the drug-coated expandable medical device is passed therethrough and that also reduces an amount of force applied by the resilient seal member onto the drug-coated expandable medical device such that a drug coating on the drug-coated expandable medical device substantially remains adhered to the drug-coated expandable medical device when passing the drug-coated expandable medical device through the reduced distal tip and through the resilient seal member;
    wherein the reduced distal tip includes one or more axially-extending slits that have a width that extends partially about the circumference of the reduced distal tip and that are configured to reduce surface contact between the reduced distal tip and the hemostasis valve;
    wherein the lumen is designed to hold the drug-coated expandable medical device while the reduced distal tip is brought into contact with and passes at least partially through the resilient seal member, the lumen also being a passageway for passing the drug-coated expandable medical device from a position proximal of the resilient seal member, through the resilient seal member, and into a body lumen; and
    wherein the proximal end region includes a proximal entry port designed to allow the drug-coated expandable medical device into the lumen and allow the drug-coated expandable medical device to be passed through the reduced distal tip, through the resilient seal member, and into the body lumen.

2. The loading tool of claim 1, wherein the one or more axially-extending slits comprises a single axially-extending slit disposed along the reduced distal tip.

3. The loading tool of claim 1, wherein the one or more axially-extending slits comprises a plurality of axially-extending slots arranged about the reduced distal tip.

4. The loading tool of claim 3, wherein at least some of the axially-extending slots extend through a tube wall of the tubular sleeve.

5. The loading tool of claim 3, wherein at least some of the axially-extending slots extend through only partially through a tube wall of the tubular sleeve.

6. The loading tool of claim 3, further comprising a stop member disposed adjacent to the axially-extending slots.

7. The loading tool of claim 1, wherein the reduced distal tip comprises a beveled distal end.

8. The loading tool of claim 1, wherein the tubular sleeve comprises a tubular body having a first section and a second section separable from the first section, the second section having a flared distal end region, the first section including the reduced distal region with a smaller outer diameter than an outer diameter of the flared distal end region of the second section.

9. The loading tool of claim 1, wherein the drug-coated expandable medical device comprises a drug-coated balloon.

10. The loading tool of claim 1, wherein the drug-coated expandable medical device comprises a drug-coated stent.

11. A medical device assembly, comprising:
    a balloon catheter having an expandable balloon;
    a stent disposed along the balloon catheter;
    a drug coating disposed along the stent;
    a loading tool disposed about the stent; and
    wherein the loading tool comprises:
        a tubular sleeve having a distal end region, a proximal end region, and a lumen extending therethrough,
        wherein the distal end region includes a reduced distal tip designed to interact with a hemostasis valve having a resilient seal member while reducing surface contact between the reduced distal tip and the hemostasis valve, the reduced distal tip including a plurality of axially-extending slits having a structure with a width extending at least partially about the circumference of the reduced distal tip such that the remainder of the reduced distal tip has a reduced dimension that allows the reduced distal tip to be passed into a proximal end of the hemostasis valve in such a way that reduces displacement of the resilient seal member while the stent is passed therethrough and that also reduces an amount of force applied by the resilient seal member onto the stent such that the drug coating on the stent substantially remains adhered to the stent device when passing the stent through the reduced distal tip and through the resilient seal member, wherein the lumen is designed to hold the stent while the reduced distal tip is brought into contact with and passes at least partially through the resilient seal member, the lumen also being a passageway for passing the stent from a position proximal of the resilient seal member, through the resilient seal member, and into a body lumen, and wherein the proximal end region includes a proximal entry port designed to allow the balloon into the lumen and allow the stent to be passed through the reduced distal tip, through the resilient seal member, and into the body lumen.

* * * * *